United States Patent
Koch et al.

(10) Patent No.: US 9,446,344 B2
(45) Date of Patent: *Sep. 20, 2016

(54) PRESSURE SWING ADSORPTION METHOD

(75) Inventors: Achim Koch, Moosburg (DE); Michael Zavrel, Olching (DE); Christoph Kröhnke, Munich (DE); Ulrich Kettling, Munich (DE)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 163 days.

This patent is subject to a terminal disclaimer.

(21) Appl. No.: 14/125,027

(22) PCT Filed: Jun. 1, 2012

(86) PCT No.: PCT/EP2012/060376
§ 371 (c)(1),
(2), (4) Date: Jul. 22, 2014

(87) PCT Pub. No.: WO2012/168154
PCT Pub. Date: Dec. 13, 2012

(65) Prior Publication Data
US 2014/0326138 A1 Nov. 6, 2014

(30) Foreign Application Priority Data

Jun. 10, 2011 (EP) ..................................... 11004796

(51) Int. Cl.
*B01D 53/047* (2006.01)
*B01D 53/04* (2006.01)
(Continued)

(52) U.S. Cl.
CPC ............. *B01D 53/047* (2013.01); *B01D 53/04* (2013.01); *C07C 29/76* (2013.01); *B01D 53/02* (2013.01);
(Continued)

(58) Field of Classification Search
CPC .... B01D 53/02; B01D 53/04; B01D 53/047; B01D 2253/108; B01D 2253/202; B01D 2253/25; B01D 2257/704; B01D 2257/70; Y02E 50/17; C07C 29/76; C07C 31/08
USPC ......................... 95/96, 141, 900, 902; 96/153
See application file for complete search history.

(56) References Cited

U.S. PATENT DOCUMENTS 3,953,566 A * 4/1976 Gore ....................... B01D 71/36
264/127
4,810,381 A * 3/1989 Hagen ................. B01J 20/28028
210/502.1

(Continued)

FOREIGN PATENT DOCUMENTS

EP 0 357 832 A1 3/1990
EP 0 443 853 A2 8/1991
(Continued)

*Primary Examiner* — Frank Lawrence
(74) *Attorney, Agent, or Firm* — Gianna J. Arnold; Saul Ewing LLP

(57) ABSTRACT

The invention describes a method for enriching at least one component from a gaseous mixture of substances, comprising the steps of (i) contacting a flow of a first gaseous mixture of substances which contains at least one component to be enriched, with a composite material at a first pressure p1 such that the at least one component to be enriched is adsorbed to the composite material and a charged composite material is obtained, said composite material comprising (a) a porous matrix of a fluorine-containing polymer having a percentage of tetrafluoroethylene monomer units of at least 95 mol % based on the total number of monomer units and (b) zeolite particles which are embedded in the matrix and around which matrix filaments extend; (ii) disrupting the flow of the gaseous mixture of substances and (iii) desorbing the at least one component to be enriched from the charged composite material by reducing the pressure to a pressure p2, with p1−p2≥200 mbar, such that a second gaseous mixture of substances is produced and removing the second gaseous mixture of substances from the composite material.

19 Claims, 1 Drawing Sheet

(51) Int. Cl.
*C07C 29/76* (2006.01)
*B01D 53/02* (2006.01)

(52) U.S. Cl.
CPC ... *B01D 2253/108* (2013.01); *B01D 2253/202* (2013.01); *B01D 2253/25* (2013.01); *B01D 2257/704* (2013.01); *Y02E 50/17* (2013.01)

(56) References Cited

U.S. PATENT DOCUMENTS

| | | | |
|---|---|---|---|
| 2002/0170436 A1* | 11/2002 | Keefer | B01J 20/183 96/121 |
| 2003/0045734 A1 | 3/2003 | Weisbeck et al. | |
| 2003/0101866 A1 | 6/2003 | Noack | |
| 2004/0069144 A1* | 4/2004 | Wegeng | C01B 3/56 95/106 |
| 2004/0118287 A1* | 6/2004 | Jaffe | B01D 53/0423 96/121 |
| 2009/0200236 A1 | 8/2009 | Diefenbacher et al. | |
| 2012/0247330 A1* | 10/2012 | Chang | B01D 53/02 95/92 |
| 2015/0065757 A1* | 3/2015 | Koch | B01D 67/0079 568/917 |

FOREIGN PATENT DOCUMENTS

| | | |
|---|---|---|
| WO | WO-01/80981 A1 | 11/2001 |
| WO | WO-2007/144247 A1 | 12/2007 |

\* cited by examiner

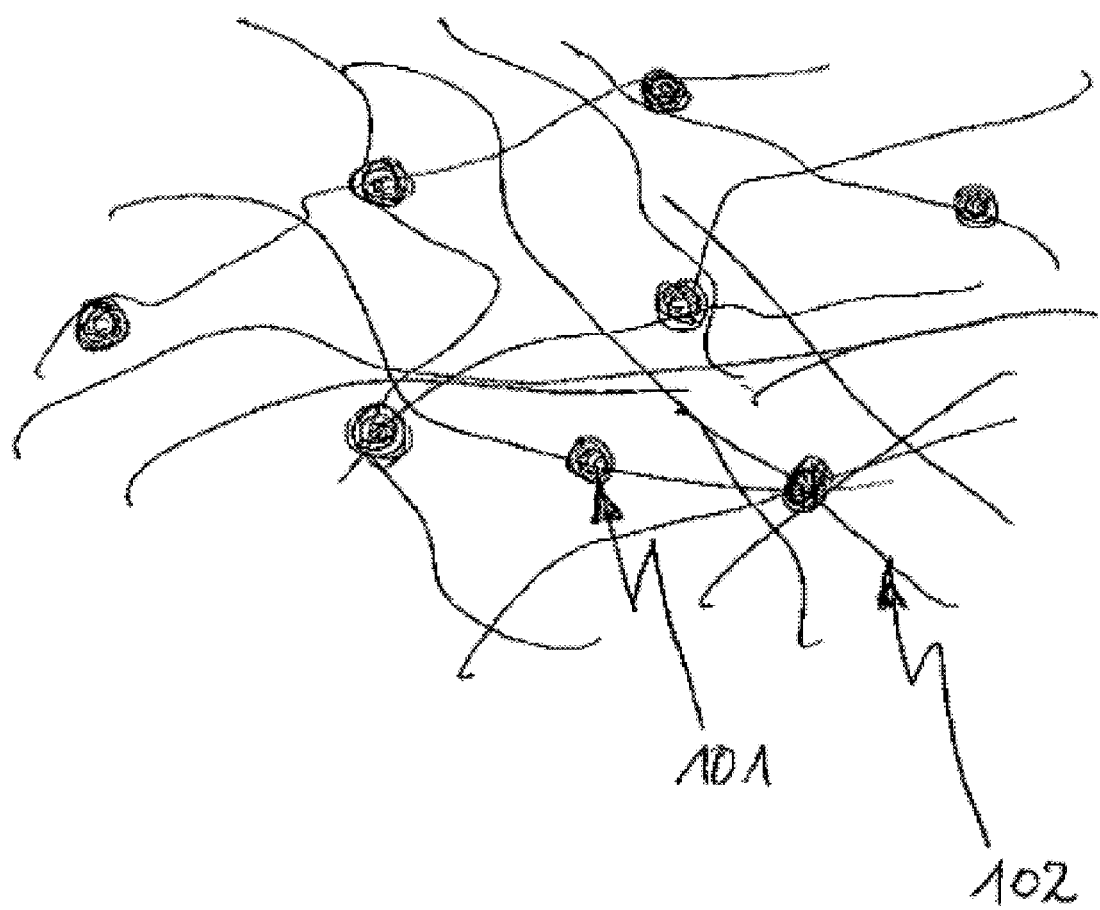

PRESSURE SWING ADSORPTION METHOD

RELATED APPLICATIONS

This application is a 35 U.S.C. §371 national stage filing of International Application No. PCT/EP2012/060376, filed Jun. 1, 2012, which claims the benefit of European Patent Application No. 11004796.6, filed Jun. 10, 2011. The entire contents of each of these applications are explicitly incorporated herein by reference.

FIELD OF THE INVENTION

The invention relates to a method for enriching at least one component from a fluid by pressure swing adsorption

BACKGROUND TO THE INVENTION

The separation of liquid or gaseous mixtures of substances with the aid of solid materials has been practised commercially and industrially for decades for a plurality of applications. Zeolites are being used more and more here due to their outstanding selectivities.

The zeolites are generally applied to carriers. The use of granules, moulded bodies or membranes is prior art. Inert solids or polymers, which together with the zeolites produce sorptively acting composite materials, are suitable as binding agents.

An example of this type of composite material is described in EP 0 773 829. Here a hydrophobic molecular sieve with a pore diameter of 5.5-6.2 angstrom is embedded into fibrillated polytetrafluoroethylene (PTFE) or blown microfibres (polyamide, polyester, polyurethane, polyolefin etc.) in a ratio of 40:1 to 1:40 as a selective sorption medium. The processing takes place with the aid of a liquid lubricant. The doughy mass is calendered biaxially, by means of which a porous film is finally produced after drying, the porosity of which can be derived from the amount of lubricant. Similar composite materials are described in the patents U.S. Pat. No. 4,153,661, U.S. Pat. No. 4,460,642 and U.S. Pat. No. 5,071,610 which likewise describe porous fibrous membranes based on PTFE for the addition of sorbents or catalytically effective particulate substances.

PTFE is particularly suitable as a matrix polymer because it can be fibrillated, is thermally stable, chemically inert and hydrophobic, i.e. it can be processed to form stable and highly flexible fibre fleeces, can be used in the working temperature range of −250 to +260° C., neither absorbs water nor is soluble; in addition, PTFE is largely inert with respect to acids and lyes. PTFE is partially crystalline and can be fibrillated above the phase transition temperature of 19° C., i.e. by applying shearing forces to PTFE power or the PTFE balls contained in the dispersion, the crystallites contained in the material can be uncoiled to form thin filaments (this effect can be observed even better above 30° C.; this is where the second phase transition of PTFE takes place). These filaments, in the best case only a few molecule layers thick, are capable, using an appropriate processing technique, of extending around, embedding and holding large quantities of filler, by means of which high-grade cross-linked, highly filled PTFE filler composites are obtained. Moreover, the polymer fibres hook and loop onto one another during the shearing, and this gives the composite material a certain degree of mechanical stability. The ability to be processed into films and moulded bodies can, however, be greatly hindered by the strong deformation forces required depending on the filler, and this is why it has proved best to use, wherever possible, lubricants (water, alcohols, crude oil distillates, hydrocarbons and other solvents) which facilitate the processing process, support the fibrillation and prevent premature destruction/tearing of the fibres due to excessive shearing. After the shaping, the solvent that has been added is generally eliminated by heating, by means of which an additional defined degree of porosity remains. By means of an optional sintering process of the PTFE material at temperatures of around 330° C., but below 360° C. (start of decomposition) the composite material obtains its final stability and shape.

Examples of the area of application for these composite materials are the membrane methods pervaporation or vapour permeation with so-called Mixed Matrix Membranes (MMMs), but also various adsorption methods, such as so-called Solid Phase Extraction (SPE) or drying methods.

Solid phase extraction is to be understood as meaning the physical separating process between a fluid and a solid phase, the component to be isolated and analysed being dissolved in a liquid or gaseous solvent. SPE has an application, for example, in analytical or preparative chromatography (e.g. High Performance Liquid Chromatography, HPLC, or Gas Chromatography, GC).

For drying methods, bulk composed of adsorption materials which adsorb water as the fluid flows through the bulk, is generally used. The best known example is the dehydration of ethanol with the aid of the hydrophilic zeolites 3A, 4A, 5A or 13X.

It is known from EP 0 773 829 that organic components from a fluid, i.e. from a liquid or a gas, can also be adsorbed.

So as to subsequently extract the components in enriched form, i.e. more highly concentrated or pure form, the organic components must be desorbed. For desorption there are the following possibilities:

First of all, the adsorbed components can be expelled by other components. However, it is a disadvantage of this method that after desorption the adsorption means is charged with the components used for the expulsion, and so further steps are required in order to remove the latter.

Secondly, the temperature of the adsorption means can be increased until the adsorbed components desorb thermally. This possibility is mentioned in EP 0 773 829. It is a disadvantage of this method, however, that as the size of the adsorber columns increases, it becomes harder and harder to introduce the heat via the adsorber walls because the wall surface to volume ratio becomes lower and lower and so less favourable. The heating of the adsorption means by means, for example, of hot flushing gas, is also associated with very large volumetric flows of the flushing gas due to the low heat capacity of gases. In addition, by means of this so-called Temperature Swing Adsorption method (TSA) short cycle times cannot generally be achieved because heating and cooling can last a very long time.

The third possibility is the so-called Pressure Swing Adsorption method (PSA) wherein the adsorbed components are desorbed by reducing the pressure. The advantage of this method is that the pressure drops very quickly and evenly in the whole adsorption column and can then be raised again. This makes very short cycle times possible. Short cycle times make it possible to reduce the required amount of adsorption means so that the adsorber columns can have clearly smaller dimensions. This reduces not only the costs for the adsorption means and the investment costs for the columns, but also reduces the operating costs of the adsorption units because shorter adsorber beds also give rise to smaller pressure losses as the gaseous mixture of substances flows through the adsorber bulk, and this must be overcome by pumps or compactors.

The disadvantage of the PSA methods, however, is that the adsorption means is subjected to frequent pressure swings, and this leads to mechanical loading of the adsorption means. The adsorption means is typically bulk composed of solid particles which rub against one another with each pressure swing so that friction occurs. Cavities formed upon granulation or deformation of the adsorption means can lead to the granules or moulded bodies breaking when there are pressure fluctuations. Furthermore, the particles may burst or break up. This can reduce the life of the adsorption means and further increase the pressure loss due to the decreasing average particle size. In order to reduce these undesired effects as far as possible, two method versions are essentially used:

(a) The pressure swings are implemented as slowly as possible, i.e. the vacuum pump is only started up slowly when tension is released, and when the pressure is increased the gaseous mixture of substances only flows into the adsorber column slowly. Accordingly, these times for the pressure swings are not available at the target pressure for adsorption or desorption. The fact that adsorption below the target pressure and desorption above the target pressure proceed less efficiently, i.e. less substance is adsorbed or desorbed per unit of time, must be compensated for by extending the cycle time. The time efficiency of the whole method is therefore disadvantageously reduced.

(b) The cycle time is extended by extending the adsorption phase and/or the desorption phase in order to reduce the number of pressure swings and so to reduce the number of procedural steps associated with strong mechanical loading of the adsorber material. However, each extension of the adsorption phase and/or of the desorption phase requires greater amounts of adsorption means, and so this has a negative impact on the cost efficiency of the method.

Therefore, the mechanical loading of the adsorption material during the pressure swing leads to a reduction of the efficiency of the method.

In summary it can be established that an optimal PSA method should use an adsorption means which has low pressure losses and makes short cycle times possible without this having any negative impact on the life of the adsorption means.

OBJECT OF THE METHOD ACCORDING TO THE INVENTION

Against the background of the prior art, it was the object of the invention to provide a method for enriching at least one component from a gas by pressure swing adsorption that in particular does not have the aforementioned disadvantages associated with the mechanical loading of the adsorber material.

DESCRIPTION OF THE METHOD ACCORDING TO THE INVENTION

Surprisingly, one was able to find that the object in question can be achieved by a method comprising the following steps:

(i) bringing a flow of a first gaseous mixture of substances which contains at least one component to be enriched into contact with a composite material at a first pressure p1 such that the at least one component to be enriched is adsorbed on the composite material and a charged composite material is obtained, said composite material comprising (a) a porous matrix of a polymer containing fluorine having a percentage of tetrafluoroethylene monomer units of at least 95 mol % based on the total number of monomer units;

(b) zeolite particles which are embedded in the matrix and around which the latter extends;

(c) optionally at least one metal material;

(d) optionally at least one further component, the amount of metal material (c) being 0 to 90% by weight based on the total weight of all of the components, the ratio of the weight of component a) to the total weight of components b) and d) being 2:98 to 25:75, and the ratio of the weight of component b) to the weight of component d) being 80:20 to 100:0;

(ii) disrupting the flow of the gaseous mixture of substances and (iii) desorbing the at least one component to be enriched from the charged composite material by reducing the pressure to a pressure p2, with p1−p2≥200 mbar, such that a second gaseous mixture of substances is formed, and removing the second gaseous mixture of substances from the composite material.

In the following the method according to the invention and preferred embodiments are described in more detail.

Step (i)

In the first step of the method a first gas mixture is guided over a composite material that contains a zeolite as an adsorber at a pressure p1.

The composite material comprises a fibrillatable polymer containing fluorine, preferably PTFE, and a zeolite which is suitable for adsorbing small molecules. In order to stiffen the material, metal in the form of metal lattice, fabric or netting, perforated or pierced metal plates can be added.

a) Matrix Composed of Polymer Containing Fluorine

The matrix of the composite material is composed of polymer containing fluorine, i.e. a homo- or copolymer having a percentage of tetrafluoroethylene monomer units of at least 95 mol %. The polymer containing fluorine can be fibrillated and can form a porous matrix by fibrillating. Moreover, the polymer containing fluorine is chemically inert and is not capable of swelling in the presence of water or organic molecules. Preferably, the polymer containing fluorine has a percentage of tetrafluoroethylene monomer units of at least 99 mol %.

Polytetrafluoroethylene (PTFE), tetrafluoroethylene hexafluoropropylene copolymer, tetrafluoroethylene chlorotrifluoroethylene copolymer, tetrafluoroethylene perfluoro-(2,2-dimethyl-1,3-dioxol)-copolymer and tetrafluoroethylene perfluoro ($C_{1-6}$-alkylvinyl ether)-copolymer such as for example tetrafluoroethylene-perfluoro(butenylvinylether)-copolymer can be specified as examples of polymer containing fluorine. PTFE is preferred.

The polymer can be used as a powder or as a dispersion. Surfactant-free PTFE powders are preferably used because the absence of any surface-active substances required for the stability of PTFE dispersions eliminates the undesired effects of the reduction of the available zeolite surface and increase of the water adsorption by such surfactants.

According to the methods described in EP 0 773 829 B1 (and the prior art documents cited in the latter) these polymers can be fibrillated, and so a porous and fibrous matrix is formed.

(b) Zeolite Particles

For the composite material according to the invention the sorbents which selectively sorb molecules from gaseous mixtures and can desorb them again under appropriate conditions are particularly suitable. Zeolites are particularly suitable for this purpose.

Furthermore, for the composite material the sorbents which are suitable for sorbing organic polar molecules from fluids containing water and desorbing them again under appropriate conditions in order to enrich or purify them are of interest. Particularly suitable for this purpose are hydrophobic zeolites, i.e. zeolites with a $SiO_2$:$Al_2O_3$ ratio of 100:1 or more, preferably 200:1 or more, more preferably 500:1 or more. These zeolites are generally very suitable for the adsorption of organic molecules such as alcohols (e.g. ethanol, butanol), ethers, ketones (e.g. acetone), aldehydes (e.g. acetal dehyde), esters (e.g. ethyl acetate), carboxylic acids (e.g. acetic acid) and carboxylic acid esters etc. The $SiO_2$:$Al_2O_3$ ratio is determined by X-ray fluorescence spectroscopy (XRF) of a sample dried for one hour at 100° C., which is then pressed with a binding agent to form a tablet, by determining the molar ratio of Si:Al which is converted to the molar ratio $SiO_2$:$Al_2O_3$.

In order to have particularly good adsorption properties, i.e. to be able to adsorb a large number of molecules per unit weight of zeolite, the zeolites should have a large surface area per unit weight determined by the BET method. Zeolites suitable for the present invention have a surface area according to the BET method of 150 $m^2$/g or larger, preferably 200 $m^2$/g or larger, and more preferably of 300 $m^2$/g or larger.

The surface area is determined by a fully automatic ASAP 2010 type nitrogen porosimeter made by the company Micromeritics using nitrogen as the adsorbed gas according to the following method according to DIN 66131 (July 1993). The sample is cooled in a high vacuum to the temperature of liquid nitrogen. Next nitrogen is continuously metered into the sample chambers. By recording the amount of adsorbed gas as a function of pressure, an adsorption isotherm is determined at constant temperature. In a pressure equalisation the analysis gas is removed step by step and a desorption isotherm is recorded. The data according to DIN 66131 (July 1993) are analysed to determine the specific surface area and the porosity according to the BET theory.

From these points of view zeolites of the silicalite, β zeolite, mordenite, Y zeolite, MFI zeolite, ferrierite (FER zeolite), dealuminated, ultrastable zeolite Y (USY zeolite) and erionite (ERI zeolite) types are preferred. The method according to the invention also allows mixtures of these zeolites.

Zeolite particles with a particle size ($d_{50}$) of 0.5 to 100 μm, more preferably of 1 to 50 μm and particularly preferably of 5 to 25 μm are preferably used. Basically, as the particle size decreases the specific surface area, i.e. the surface area per unit mass increases. A large specific surface area generally leads to a high and so advantageous adsorption speed. Since, however, the handling and processing of a powder becomes increasingly difficult and complex as the particle size decreases, it is not advantageous to choose very small particle sizes although this is possible in principle.

A single zeolite type or a mixture of a number of zeolite types can be used. The single zeolite type or the zeolite types can be used in a uniform particle size or in a number of particle sizes.

(c) Metal Material

The composite material can contain a metal material.

Suitable for the composite material according to the invention are metal materials, i.e. pure metals and alloys. Metal materials which are chemically inert in the presence of water and organic molecules, i.e. do not react, or only react to a limited degree with water and/or organic compounds, are particularly suitable. Limited reaction with water and/or organic compounds means, for example, that passivation of the surface of the metal material occurs, but not a chemical reaction which ultimately leads to total degradation of the metal material.

From these points of view, corrosion-free metals, particularly preferably stainless steels which are used in the food and chemical industry, e.g. X2CrNi1911 (material number 1.4306), X12CrNi177 (material number 1.4310), or X5CrNi1810 (material number 1.4301) are preferred.

The form in which the metal material is present in the composite material is not limited. For example, the metal material can be present in two-dimensional form, i.e. for example in the form of metal lattices, fabrics, nettings or of perforated or pierced metal plates or sheets, or in particle form, i.e. for example in the form of powders or shavings. By means of the structures specified as examples it is guaranteed that a good connection between the metal and the composite material is achieved. The metal material can be present in the composite material in a number of forms, i.e. both in particle form and in two-dimensional form.

When using the metal material in two-dimensional form a mesh width or hole opening of 0.5-5 mm, in particular 1-2 mm is preferred. The number and distribution of holes per surface unit is not especially restricted and is determined by considerations of the person skilled in the art with regard to the desired permeability and stability. Likewise, the thickness of the metal material in the two-dimensional form used is not especially restricted provided that the desired dimensional stability is achieved. For this purpose the thickness of the metal material is customarily 0.1-1 mm, preferably 0.2-0.5 mm, and particularly preferably 0.25 mm. In the composite material according to the invention the amount of optional metal material (c) is 0 to 90% by weight based on the total of all of the components of the composite material, i.e. the metal material is an optional component. When the metal material is present, the amount of metal material (c) is more than 0% by weight, but no more than 90% by weight based on the total of all of the components of the composite material. Preferably, the amount of metal material (c) is 5 to 80% by weight, more preferably 10 to 70% by weight based on the total of all of the components of the composite material.

(d) Further Components

In the composite material according to the invention one or a number of components can optionally be provided which can be chosen, for example, from auxiliary substances, surfactants, lubricants, precipitated silicic acid, silica, activated carbon, pigments, glass beads or fibres, synthetic fibres, fibres of natural origin, clay minerals such as for example bentonite.

The polymer containing fluorine (a) is in a ratio to the overall weight of the zeolite particles (b) and the optionally provided further component (d) of 2:98 to 30:70, preferably of 4:96 to 20:80, and more preferably of 5:95 to 15:85.

The ratio of the weight of the zeolite particles (b) to the weight of component (b) is 80:20 to 100:0, i.e. component (d) is optional. Preferably, the ratio of the weight of the zeolite particle (b) to the weight of component (d) is 90:10 to 100:0, and more preferably 95:5 to 100:0.

In a preferred embodiment the ratio of the weight of the polymer containing fluorine (a) to the overall weight of the zeolite particle (b) and the optionally provided further component (d) is in a range of 4:96 to 20:80, more preferably 5:95 to 15:85, the ratio of the weight of the zeolite particle (b) to the weight of component (d) being 90:10 to 100:0.

The composite material is produced by mixing components (a) and (b) and the optional metal material (c) if the metal material (c) is used in an appropriate small-part form, i.e. for example in powder form, in the amounts specified above and then by kneading, the fibrillation of the polymer and addition of the zeolite to the porous polymer matrix ensuing upon shearing [FIG. 1]. The kneading is carried out at room temperature or preferably at an increased temperature such as for example 30° C. or more, 50° C. or more or 70° C. or more because at a temperature in these ranges better processability and in particular better fibrillation of the polymer containing fluorine is generally possible. The upper temperature limit is first and foremost determined by thermal stability of the components contained in the mixture. From this point of view processing at a temperature of no more than 200° C., and more preferably of no more than 150° C. is generally preferred.

In order to achieve good miscibility of the components of the composite material, polymer (a) and zeolite (b) are preferably used in powder form. The polymer (a) can for example also be used in the form of a commercially available dispersion in water. These commercially available dispersions can contain auxiliary substances such as for example stabilisers, surfactants or other components that change the surface tension and/or other auxiliary substances.

In order to facilitate the mixing and shearing process, water or alcohol can be added as lubricants. In order to be able to largely dispense subsequently with an energy-consuming and expensive drying step one actually preferably works, however, with the smallest possible amount of liquid, i.e. no lubricant is added other than the amount of liquid introduced via the PTFE dispersion (maximum 40% of the dispersion).

After the kneading step the doughy to fleece-like product is rolled out biaxially between heated rollers (temperature 60-150° C.) in a number of steps to form a mat first of all, and then to form a film, the fibrillation being optimised and, for example, a homogeneous final layer thickness of 0.3 to 1 mm, preferably 0.4-0.6 mm being set. A heatable calender or roller system comprising at least 2 rollers, preferably 4 rollers or more, is suitable for this step.

A suitable method for producing a composite material composed of a polymer (a) and a zeolite (b) is also described in EP 0 773 829 B1 and the documents cited in the latter.

If a metal material is to be introduced in two-dimensional form, the material thus obtained is pressed in one or more steps between pressure-loaded rollers within a laminator or calender with the metal material in two-dimensional form, e.g. stainless steel mesh, such that a composite composed of at least one layer of the material and the metal material is formed. Preferably, a layer of the metal material is enclosed between two layers of the material. Preferably both layers of the material penetrate through the openings in the two-dimensional metal material, by means of which the stability of the composite is optimised. The step of connecting the metal material and the material can take place at room temperature, advantageously however at 70-250° C., in order to eliminate any residual moisture which may be present in the material, for example, due to the use of water as a lubricant when mixing and/or kneading polymer containing fluorine (a) and zeolite particles (b) as described above. A drying step optionally follows.

Optionally, one or more heating element(s) is/are introduced into the material such that the heat energy can be easily transferred from the heating element to the metal material. The metal material can optionally itself perform the function of the heating element e.g. by heating by means of magnetic induction, electric resistance heating or heat exchange. By means of the heating element the adsorption and desorption temperature can be optimised within the framework of the process yield. It serves, moreover, to facilitate the optionally necessary regeneration of the material.

The composite material can be used in any form. For example, the composite material can be arranged in the form of a folded film or a film wound like a spiral or in the form of bulk comprising a plurality of moulded bodies or particles so as to be brought into contact with the flow of the first gaseous mixture of substances. Different forms can also be used in combination. The arrangement of the composite material in the flow of the first gaseous mixture of substances will also be referred to as "packing" in the following.

The first gaseous mixture of substances contains at least one component to be enriched. This component can be organic or non-organic and can be enriched with respect to further components which are organic or non-organic.

The at least one component to be enriched is, for example, an organic substance, for example from one of the substance-class alcohols (e.g. ethanol, butanol), ethers (e.g. methyl tert butyl ether or tetrahydrofuran), ketones (e.g. acetone), aldehydes (e.g. acetaldehyde), esters (e.g. ethyl acetate) and carboxylic acids (in particular $C_{1-4}$ carboxylic acids such as e.g. acetic acid or propionic acid).

As a non-organic component the gaseous mixture of substances can contain, for example, water. Hydrogen sulphide, ammonia, hydrogen, carbon dioxide, oxygen or nitrogen can also be present in the gaseous mixture of substances as non-organic components Preferably, the first gaseous mixture of substances is a mixture of substances that is obtained by gas stripping an aqueous solution with volatile organic compounds of the substance classes specified above. The aqueous solution is particularly preferably a fermentation solution in which at least one of the aforementioned organic substances is produced fermentatively or enzymatically, very particularly preferably a fermentation solution which is obtained by ethanolic fermentation by means of yeasts or bacteria or by so-called ABE fermentation by means of bacteria. In so-called ABE fermentation acetone, butanol and ethanol (ABE) are produced by means of bacteria. This gas stripping is particularly preferably implemented in situ, in situ meaning that the gas stripping takes place during fermentation. However, the gas stripping can also take place after the fermentation is completed. The gas stripping can take place in an external gas stripping apparatus connected to the fermenter.

The adsorption takes place at a higher pressure (p1) than desorption. The pressure during adsorption is for example in the range of 0.4 to 20 bar, preferably in the range of 0.6 to 10 bar, particularly preferably in the range from 0.8 to 5 bar, and very particularly preferably in the range from 1 to 2.5 bar.

The temperature of the gas flow upon bringing into contact with the composite material is between 0 and 250° C., preferably between 10 and 200° C., particularly preferably between 20 and 150° C. and very particularly preferably between 30 and 100° C.

Preferably, the flow velocity of the first gaseous mixture of substances is set so that a volumetric flow when the first gaseous mixture of substances is brought into contact with the composite material in step (i) that corresponds to a superficial velocity of 0.5 m/s or more is achieved. More preferably, the flow velocity of the first gaseous mixture of substances is set so that a volumetric flow that corresponds to a superficial velocity of 0.75 m/s or more, particularly preferably 1.0 m/s or more, is achieved when the first gaseous mixture of substances is brought into contact with the composite material in step (i).

The flow of the first gaseous mixture of substances is guided over the packing of the composite material until desired charging is achieved. This desired charging does not have to be specifically determined but, for example, the flow of the first gaseous mixture of substances can be guided over the packing of the composite material for a specific period of time that seems suitable.

Step (ii)

When the desired charging of the composite material is achieved, the flow of the first gaseous mixture of substances is disrupted.

Step (iii)

By means of this step the at least one component to be enriched is desorbed from the composite material and the composite material is thus prepared for implementation of step (i) again. By the desorption of the at least one component to be enriched from the composite material, a second gaseous mixture of substances is formed with the atmosphere that surrounds the composite material during desorption.

The desorption of the at least one component to be enriched takes place at a lower pressure (p2) than the adsorption in step (i). The pressure difference (p1–p2) between the adsorption and the desorption step is at least 200 mbar, preferably at least 500 mbar and particularly preferably at least 800 mbar.

In a preferred embodiment of the method according to the invention a flushing gas is used during the desorption, i.e. the at least one component to be enriched, which is desorbed from the composite material, is flushed out of the packing of the composite material by a gas (the flushing gas) guided over the composite material. Preferred flushing gases are inert gases, and particularly preferably the flushing gases are air, carbon dioxide, nitrogen, noble gases or mixtures of the latter. In a further embodiment of the method according to the invention the flushing gas contains water. Particularly preferably the temperature of the flushing gas is above the temperature of the adsorption means.

Preferably, the flow direction of the second gaseous mixture of substances is opposite to the flow direction of the first gaseous mixture of substances in step (i).

In a further embodiment of the method according to the invention a hybrid form of PSA and TSA is used, i.e. such that the desorption does not take place purely by reducing the pressure, but by the supporting introduction of thermal energy. This supporting introduction of thermal energy can take place by introducing hot flushing gas or by heating via the column wall, via heating coils within the adsorber column or the packing of the composite material or by combinations of all three options. If a metal material (c) is present in the composite material in a two-dimensional form, thermal energy can also be introduced by heating the metal material, for example by magnetic induction, electric resistance heating or by heat exchange. If a metal material (c) is present in the composite material in particle form, the thermal energy can also be introduced by heating the metal material, for example by magnetic induction or by heat exchange.

The number of pressure swings between p1 and p2 is preferably at least 1 per hour, more preferably at least 2 per hour and particularly preferably at least 3 per hour.

The average velocity at which the pressure swing between p1 and p2 is implemented is preferably 40 mbar/min or more, more preferably 100 mbar/min or more, particularly preferably 200 mbar/min or more.

BRIEF DESCRIPTION OF THE FIGURE

FIG. 1 sketches the PTFE zeolite composite material that is used in the method according to the invention (101=zeolite particles, 102=net-like PTFE fibrillae).

EXAMPLES

The method according to the invention is described by means of the following non-restrictive examples:

Example 1

Production of a PTFE Zeolite Composite Material

PTFE dispersion TE3893-N (approx. 60% PTFE content, DuPont) with a PTFE percentage by weight of 10% together with a zeolite (ZSM-5, H form; $SiO_2/Al_2O_3$>800; manufacturer: SÜML ud-Chemie AG, Germany) is produced by mixing the individual materials and then kneading for an hour in a Werner & Pfleiderer LUK 075 laboratory kneader at 80-130° C., fibrillation of the PTFE and addition of the zeolite ensuing upon shearing.

After the kneading step the fleece-type product is rolled out between heated rollers (temperature 70° C.) in a number of steps biaxially to a film, the fibrillation being optimised and a homogenous layer thickness of 0.5 mm being set. A calender system made by the company Fetzel is suitable for this step.

Example 2

Adsorption of Ethanol From a Gas Flow 500 ml of a 5% (w/v) ethanol water solution were stripped for 24 hours with a volumetric flow of 1 l/min. A membrane pump (KNF, Germany), volumetric flow regulator (Swagelok, Germany) and a gas washing bottle (VWR, Germany) were used. The gas flow was conveyed through a glass column (VWR, Germany) which was packed with the composite material from Example 1. The gas flow was conveyed back into the gas washing bottle within the framework of a circulation process so that the system was closed. The glass column was heated to 40° C. by a heating sleeve (Mohr & Co GmbH, Germany). The gas stripping in the gas washing bottle took place at 30° C. After the end of the experiment the ethanol concentration in the solution was determined by gas chromatography (Trace GC, ThermoFischer, Germany). Moreover, the change in weight of the zeolite and the solution was determined. The charging of the zeolite with water and ethanol and from this the percentage of water and the percentage of volatile organic compound ethanol were calculated by a mass balance.

Example 3

Ad- and Desorption of Ethanol by Pressure Swings 500 ml of a 5% (w/v) ethanol water solution were stripped for 24 hours with a volumetric flow of 1 l/min. A membrane pump (KNF, Germany), a volumetric flow regulator (Swagelok, Germany) and a gas washing bottle (VWR, Germany)

were used. The gas flow was conveyed through a glass column (VWR, Germany) which was packed with 101.7 g of the composite material from Example 1. The gas flow was conveyed back into the gas washing bottle within the framework of a circulation process so that the system was closed. The glass column was heated to 40° C. by a heating sleeve (Mohr & Co GmbH, Germany). The gas stripping in the gas washing bottle took place at 30° C. After adsorption desorbing took place by means of a vacuum pump (CVC3000 type: VacuuBrand, Germany) at 50 mbar. The desorbate was condensed in a cooling trap cooled with liquid nitrogen.

Example 4

Pressure Loss

The two materials from Examples 2 and 3 were compared with one another as regards pressure loss. For this purpose glass columns with a diameter of 30 mm were packed with both materials respectively, the bulk height in both cases being 290 mm Next a flow of gas, which corresponded to a superficial gas velocity of 1 m/s, was conveyed through the column. The pressure was measured in front of the column with a pressure sensor; atmospheric pressure prevailed behind the column. The pressure difference corresponds to the pressure loss of the packing.

With the PTFE zeolite material the pressure loss calculated up to the nearest meter was 7.5 mbar, and with the zeolite granules 153.5 mbar. Therefore, the pressure loss of the PTFE zeolite material was less than 5% of the granule bulk. Even if one standardised to the same mass of adsorption means, the pressure loss of the PTFE zeolite material was less than 7.5% of the granule bulk.

The invention claimed is:

1. A method for enriching at least one component from a gaseous mixture of substances, comprising:
    (i) bringing a flow of a first gaseous mixture of substances which contains at least one component to be enriched into contact with a composite material at a first pressure p1 such that the at least one component to be enriched is adsorbed on the composite material and a charged composite material is obtained, said composite material comprising:
        (a) a porous matrix of a polymer containing fluorine having a percentage of tetrafluoroethylene monomer units of at least 95 mol % based on the total number of monomer units;
        (b) zeolite particles which are embedded in the matrix and around which the latter extends, said zeolite particles having a $SiO_3:Al_2O_3$ ratio of at least 200:1;
        (c) at least one metal material;
        (d) optionally at least one further component, wherein: the amount of metal material (c) is 1 to 90% by weight based on the total weight of all of the components, the ratio of the weight of component (a) to the total weight of components (b) and (d) is 2:98 to 25:75, and the ratio of the weight of component (b) to the weight of component (d) is 80:20 to 100:0;
    (ii) disrupting the flow of the gaseous mixture of substances and
    (iii) desorbing the at least one component to be enriched from the charged composite material by reducing the pressure to a pressure p2, with p1−p2≥200 mbar, such that a second gaseous mixture of substances is formed, and removing the second gaseous mixture of substances from the composite material.

2. The method according to claim 1, wherein the concentration of the at least one component to be enriched is higher in the second gaseous mixture of substances formed in step (iii) than in the first gaseous mixture of substances.

3. The method according to claim 1, wherein the zeolite is a hydrophobic zeolite.

4. The method according to claim 1, wherein the at least one component to be enriched in the first gaseous mixture of substances is an organic component.

5. The method according to claim 1, wherein the gaseous mixture of substances containing water and at least one organic component is chosen from the group consisting of alcohols, ethers, ketones, carboxylic acids, carboxylic acid esters and aldehydes as the component to be enriched.

6. The method according to claim 1, wherein the ratio of the weight of component (a) to the total weight of components (b) and (d) is 4:96 to 20:80.

7. The method according to claim 1, wherein the ratio of the weight of component (a) to the total weight of components (b) and (d) is 5:95 to 15:85.

8. The method according to claim 1, wherein the amount of metal material (c) is 5 to 80% based on the total weight of all of the components.

9. The method according to claim 1, wherein the amount of metal material (c) is 10 to 70% by weight based on the total weight of all of the components.

10. The method according to claim 3, wherein the zeolite is chosen from the group consisting of silicalite, β zeolite, mordenite, Y zeolite, MFI zeolite, ferrierite (FER zeolite), dealuminated, ultrastable zeolite Y (USY zeolite) and erionite (ERI zeolite) and mixtures of the latter.

11. The method according to claim 1, wherein p1−p2>500 mbar.

12. The method according to claim 1, wherein the swing between pressure p1 and pressure p2 takes place at an average speed of 40 mbar/min or more.

13. The method according to claim 1, wherein the swing between pressure p1 and pressure p2 takes place at an average speed of 100 mbar/min or more.

14. The method according to claim 1, wherein the flow direction of the second gaseous mixture of substances in step (iii) is opposite to the flow direction of the first gaseous mixture of substances in step (i).

15. The method according to claim 1, wherein the bringing into contact in step (i) takes place with a volumetric flow which corresponds to a superficial velocity of 0.5 m/s or more.

16. The method according to claim 1, wherein the bringing into contact in step (i) takes place with a volumetric flow which corresponds to a superficial velocity of 0.75 m/s or more.

17. The method according to claim 1, wherein the number of pressure swings between p1 and p2 is at least 1 per hour.

18. The method according to claim 1, wherein the number of pressure swings between p1 and p2 is at least 2 per hour.

19. The method according to claim 1, said zeolite particles having a $SiO3:Al2O3$ ratio of at least 500:1.

* * * * *